(12) United States Patent
Klimberg et al.

(10) Patent No.: US 7,769,432 B2
(45) Date of Patent: Aug. 3, 2010

(54) MINIMALLY INVASIVE DIAGNOSIS AND TREATMENT FOR BREAST CANCER

(75) Inventors: V. Suzanne Klimberg, Little Rock, AR (US); Sohelia Korourian, Little Rock, AR (US); Steven Harms, Fayetteville, AR (US); Gal Shafirstein, Little Rock, AR (US)

(73) Assignee: Board of Trustees of the University of Arkansas, Little Rock, AR (US)

( * ) Notice: Subject to any disclaimer, the term of this patent is extended or adjusted under 35 U.S.C. 154(b) by 1608 days.

(21) Appl. No.: 10/866,913

(22) Filed: Jun. 14, 2004

(65) Prior Publication Data

US 2005/0000525 A1 Jan. 6, 2005

Related U.S. Application Data

(63) Continuation-in-part of application No. 10/306,117, filed on Nov. 27, 2002, now Pat. No. 6,978,788.

(60) Provisional application No. 60/337,626, filed on Dec. 10, 2001.

(51) Int. Cl.
*A61B 6/00* (2006.01)
*A61B 8/00* (2006.01)

(52) U.S. Cl. .................. 600/473; 600/439; 606/21; 606/27

(58) Field of Classification Search ............ 600/421, 600/567, 473, 439; 128/898; 606/21, 27
See application file for complete search history.

(56) References Cited

U.S. PATENT DOCUMENTS

| | | | | |
|---|---|---|---|---|
| 5,697,902 A | * | 12/1997 | Goldenberg | 604/500 |
| 5,699,798 A | * | 12/1997 | Hochman et al. | 600/420 |
| 6,375,634 B1 | * | 4/2002 | Carroll | 604/19 |
| 6,391,026 B1 | * | 5/2002 | Hung et al. | 606/41 |
| 6,427,081 B1 | * | 7/2002 | Burbank et al. | 600/431 |
| 6,494,844 B1 | * | 12/2002 | Van Bladel et al. | 600/567 |
| 6,602,204 B2 | * | 8/2003 | Dubrul et al. | 600/567 |
| 6,714,808 B2 | * | 3/2004 | Klimberg et al. | 600/411 |
| 6,725,095 B2 | * | 4/2004 | Fenn et al. | 607/101 |
| 6,743,228 B2 | * | 6/2004 | Lee et al. | 606/47 |
| 6,961,602 B2 | * | 11/2005 | Fuimaono et al. | 600/374 |

(Continued)

OTHER PUBLICATIONS

Shirley, Suzanne E. D.M. Usefulness of Touch Preparation Cytology in Postmortem Diagnosis: A Study From the University Hospital of the West Indies: The Internet Journal of Pathology. 2005; vol. 3 No. 2.*

(Continued)

*Primary Examiner*—Eric F Winakur
*Assistant Examiner*—Helene Bor
(74) *Attorney, Agent, or Firm*—Benjamin Aaron Adler (57) ABSTRACT

The present invention provides a treatment method to excise a cancerous lesion, such as in the breast, with subsequent ablation of the margin. The method provides for location and excision with ablation under open guidance or guided imaging and for diagnosis by cytology. The method may be a minimally, invasive same day method with diagnosis before or immediately after excision. Also provided is a method of treating close or positive margins of an excisional site of a cancerous lesion in a breast by ablating the margin while monitoring the fluorescence of a fluorophor at the site to determine when ablation of the close or positive margin has occurred.

27 Claims, 3 Drawing Sheets

U.S. PATENT DOCUMENTS

| | | | |
|---|---|---|---|
| 7,025,765 B2* | 4/2006 | Balbierz et al. | 606/41 |
| 2002/0026127 A1* | 2/2002 | Balbierz et al. | 600/567 |
| 2002/0026188 A1* | 2/2002 | Balbierz et al. | 606/41 |
| 2002/0052545 A1* | 5/2002 | Klimberg et al. | 600/410 |
| 2002/0077627 A1* | 6/2002 | Johnson et al. | 606/41 |
| 2002/0161298 A1* | 10/2002 | Burbank et al. | 600/431 |
| 2003/0039959 A1* | 2/2003 | Love et al. | 435/6 |
| 2003/0049262 A1* | 3/2003 | Love et al. | 424/155.1 |
| 2003/0109871 A1* | 6/2003 | Johnson et al. | 606/42 |
| 2003/0212394 A1* | 11/2003 | Pearson et al. | 606/41 |
| 2003/0225362 A1* | 12/2003 | Currie et al. | 604/20 |
| 2004/0224347 A1* | 11/2004 | Love et al. | 435/6 |
| 2006/0241577 A1* | 10/2006 | Balbierz et al. | 606/32 |

OTHER PUBLICATIONS

Prozyme. Glossary of Terms. http://www.prozyme.com. 2005. Accessed Jul. 3, 2007.*

Bilchik et al. Cryosurgical Ablation and Radiofrequency Ablation for Unresectable Hepatic Malignant Neoplasms: A Proposed Algorithm. Arch Surg vol. 135 Jun. 2000. p. 657-664.*

* cited by examiner

MINIMALLY INVASIVE DIAGNOSIS AND TREATMENT FOR BREAST CANCER

CROSS-REFERENCE TO RELATED APPLICATION

This application is a continuation-in-part of non-provisional U.S. Ser. No. 10/306,117, filed Nov. 27, 2002, now U.S. Pat. No. 6,978,788 which claims benefit of provisional U.S. Ser. No. 60/337,626, filed Dec. 10, 2001, now abandoned.

BACKGROUND OF THE INVENTION

1. Field of the Invention

The present invention relates generally to the field of cancer treatment. More specifically, the present invention relates to a method of diagnosis and treatment for cancer such as breast cancer by combining techniques of tumor excision and margin ablation.

2. Description of the Related Art

Breast cancer will be diagnosed in approximately one in eight women in their lifetime and one in 30 will die of this disease. It is the leading cause of cancer deaths in women 40-55 years of age and the second leading cause of cancer deaths in women overall. Breast cancer does occur in males, but is much less common.

It is desirable and often necessary to perform procedures of detecting, sampling, and testing lesions and other abnormalities in the tissues of humans and other animals for pre-malignant conditions. This is particularly important in the diagnosis and treatment of patients with cancerous tumors. Typically, in the case of cancer, when a physician establishes by means of known procedures, i.e. palpation, mammography, x-ray, MRI, or ultrasound imaging, that suspicious circumstances exist, a biopsy is performed to determine whether the cells are cancerous. A biopsy is indicated if suspicious tissue is detected. Five out of six biopsies performed return benign indications.

Biopsy may be an open or percutaneous technique. Open biopsy removes the entire mass in an excisional biopsy or a part of the mass in an incisional biopsy. Percutaneous biopsy, on the other hand, usually is done with a needle-like instrument and may be either a fine needle aspiration (FNA) or a core biopsy. In fine needle aspiration biopsy, very small needles are used to obtain individual cells or clusters of cells for cytologic examination. The cells may be prepared such as in a Papanicolaou (Pap) smear. In core biopsy, as the term suggests, a core or fragment of tissue is obtained for histologic examination, which may be done via a frozen section or paraffin section. The chief difference between fine needle aspiration and core biopsy is the size of the actual tissue core taken. An imaging system having spectroscopic capabilities, such as the stereotactic guidance system described in U.S. Pat. No. 5,240,011, is employed to guide the extraction instrument to the lesion.

Depending on the procedure being performed, the suspicious lesion may be partially or completely removed. Visibility of the lesion by the imaging system may be hampered because of the distortion created by the extraction process itself as well as associated bleeding in the surrounding tissues. Although the lesion is removed and all fluids are continuously aspirated from the extraction site, it is likely that the process will "cloud" the lesion, thus impairing exact recognition of its margins. This makes it difficult to ensure that the entire lesion will be removed.

Often, the lesion is merely a calcification derived from tissue, which may be cancerous or precancerous, and, therefore, it is desirable to remove only a sample of the lesion rather than the entire lesion. Such a lesion actually serves to mark or define the location of adjacent abnormal tissue, so the physician does not wish to remove the entire lesion and, thereby, lose a critical means for later relocating the affected tissue. One of the benefits to the patient from core biopsy is that the mass of the tissue taken is small. However, oftentimes, either inadvertently or because the lesion is too small, the entire lesion is removed for evaluation, even though it is desirable to remove only a portion. Thus, if subsequent analysis indicates the tissue to be malignant, it is difficult for the physician to determine the precise location of the lesion in order to perform necessary additional procedures on adjacent potentially cancerous tissue.

A number of procedures and devices for marking and locating particular tissue locations are known in the prior art. For example, location wire guides, such as described in U.S. Pat. No. 5,221,269, are well known for locating lesions, particularly in the breast. The device comprises a tubular introducer needle and an attached wire guide that has at its distal end a helical coil configuration for locking into position about the targeted lesion.

The needle is introduced into the breast and guided to the lesion site using an imaging system of a known type, for example, x-ray, ultrasound or magnetic resonance imaging (MRI), at which time the helical coil at the distal end is deployed about the lesion. The needle may then be removed from the wire guide which remains in a locked position distally about the lesion for guiding a surgeon down the wire to the lesion site during subsequent surgery. While such a location system is effective, it is obviously intended and designed to be only temporary and is removed once the surgery or other procedure has been completed.

Other devices are known for marking external regions of a patient's skin. For example, U.S. Pat. No. 5,192,270 discloses a syringe that dispenses a colorant to give a visual indication on the surface of the point at which an injection has or will be given. Similarly, U.S. Pat. No. 5,147,307 discloses a device which has patterning elements for impressing a temporary mark in a patient's skin for guiding the location of an injection or the like. It is also known to tape or otherwise adhere a small metallic marker, e.g. a 3 millimeter diameter lead sphere, on the skin of a human breast in order to delineate the location of skin calcifications. Obviously, however, none of these approaches are useful for marking and delineating internal tissue abnormalities, such as lesions, tumors or margins.

A method of identifying and treating abnormal neoplastic tissue or pathogens within the body is described in U.S. Pat. No. 4,649,151. In this method a tumor-selective photosensitizing drug is introduced into a patient's body where it is cleared from normal tissue faster than it is cleared from abnormal tissue. After the drug clears normal tissue, but before it has cleared abnormal neoplastic tissue, the abnormal neoplastic tissue may be located by the luminescence of the drug within the abnormal tissue.

The fluorescence may be observed with low intensity light, some of which is within the drug's absorbency spectrum. Once detected, the tissue may be destroyed by further application of higher intensity light having a frequency within the absorbency spectrum of the drug. Of course, this method also is only a temporary means for marking the abnormal tissue. Additionally, once the abnormal tissue has been destroyed during treatment, the marker is destroyed as well.

It is also known to employ biocompatible dyes or stains to mark breast lesions. First, a syringe containing the colorant is guided to a detected lesion by an imaging system. Later, during the extraction procedure, the surgeon harvests a tissue sample from the stained tissue. However, while such staining techniques can be effective, it is difficult to precisely localize the stain. Also, the stains are difficult to detect using fluorescence imaging and may not be permanent.

In considering other treatment alternatives for breast cancer, surgeons treating both benign and malignant breast abnormalities have taken great interest in the advantages of percutaneous ablation over open surgical excision. Several small pilot trials attempting to treat fibroadenomas or small breast cancers with cryosurgery, laser ablation or radiofrequency have been reported. These ablative techniques employ freezing or indirect heat to ultimately induce cell death. Thermally-induced apoptosis impairs adequate pathologic assessment of tumor grade, lymphovascular invasion and biologic tumor markers, i.e., estrogen, progesterone and HER-2/neu, therefore necessitating a pre-ablative size assessment and histologic diagnosis via core bipsy.

Cryoablation creates an iceball in an elliptical fashion around the lesion with argon gas. The duration of the freezing cycle to create an adequately sized iceball is proportional to the size of the lesion. This cryoablative technique is visualized with real time ultrasound to monitor both the growth of the iceball, as well as its proximity to overlying skin or underlying pectoralis muscle. Currently the only FDA-approved indication for cryoablation is the treatment of a core biopsy proven fibroadenoma.

Using this technique 57 fibroadenomas were cryoablated in an office-based setting with only local anesthetic (1). This demonstrated that these lesions progressively shrink, eventually taking 12 months or more to completely resolve. The fact that a biopsy is obtained for pathologic concordance prior to any ablative process and that percutaneous excision via vacuum-assisted biopsy can be accomplished on the same visit in about 15 minutes seems to have pre-empted any ablative technique for benign purposes (2).

Multiple groups are studying the efficacy of cryotherapy in ablating small invasive carcinoma. It appears that the size of the cryoprobe may influence the ability to completely ablate different size cancers. In one study, 5 out of 16, i.e., 31%, 16 mm invasive breast cancers were ablated completely with a 3 mm probe (3). When patients with tumors $\geq 23$ mm were treated, incomplete necrosis was seen in all excised specimens.

The cryoprobe has been used as an alternative method to needle localization to better obtain negative margins when excising non-palpable lesions (4). The cryoprobe was used to create an iceball that engulfed the non-palpable lesion plus an additional 5-10 mm of breast tissue surrounding the lesion. This technique made non-palpable lesions palpable, hence obviating the need for needle localization. By including a rim of adjacent normal breast tissue in the cryoprobe-generated iceball, the need for re-excision secondary to positive margins was reduced to 5.6%.

Laser ablation induces apoptosis by directing a specific wavelength of light into a narrow beam of high intensity light containing energy. This generated energy produces heat at the tip of the laser. Laser requires precise targeting with either MRI or stereotactic guidance to ablate a specific limited area. An MRI-guided laser was used in 12 patients to ablate completely breast tumors less than 3 cm prior to conventional surgical treatment (5). In three cases, simultaneous laser fibers were used to create a composite zone of ablation which successfully ablated these larger lesions. In 9 cases, portions of a larger mass were selected for ablation.

Stereotactic guidance has been examined during laser ablation of mammographic-detected small breast cancers for several years (6). The coordinates identifying the center of the lesion are stereotactically obtained and the laser fiber is inserted into this position using a 16 gauge needle. A multi-sensor thermal needle at the periphery of the lesion monitors tissue temperature. Tissue temperature of 50°-55° C. induces cellular death (7-8).

After implementing technical and procedural changes, the success rate for complete tumor ablation in two groups of 14 patients was 93% and 100%. The upper size criteria of a tumor or of a cluster of microcalcifications associated with ductal carcinoma in situ (DCIS) treated in these groups was $\leq 1.5$ cm measured on ultrasound or diagnostic mammogram. The limitation on lesion size is due to the range of zone of ablation created by the laser. Typically the coagulative zone ranges 2.5-3.0 cm in diameter allowing for 0.5 cm negative margin circumferentially around the lesion (9).

Radiofrequency ablation is the most studied ablative technique. This technique utilizes alternating high-frequency current to agitate tissue ions between the prongs of a single probe. This agitation results in frictional heat to ultimately induce coagulative necrosis.

A multi-institutional study was conducted in which 20 patients with T1 breast carcinoma underwent intraoperative radiofrequency ablation followed by surgical excision (10). Complete ablation was found in 87% of patients using nicotinamide adenine dinucleotide staining. Incomplete ablation in four patients was thought due to the inability to adequately size the tumor with standard preoperative imaging or secondary to inappropriate targeting via ultrasound. In another study, both pre- and post-radiofrequency ablation with breast MRI used (11). The addition of MRI not only accurately assesses the local extent of disease preoperatively but also enables visualization of the zone of ablation, which differs from the intensity of residual carcinoma.

Recent trends in breast cancer treatment favor breast conservation surgery, with an emphasis on improved cosmetic results. However, prior to surgery, the patients must wait for pathology results of a biopsy before a final diagnosis can be given. Further waiting is required before the patients can be treated for removal of a malignant lesion. Moreover, breast conservation surgery via lumpectomy often results in some deformity and requires repeated surgery to establish a clear margin around the malignant lesion.

None of the presently available devices for excision adequately excise a margin, i.e., a tumor-free zone. Additionally, no work has been published on ablation of tumor bed margin after excision. Thus, there is a need in the art for improved, minimally-invasive methods of treating cancers or lesions resulting in established clear, negative margins. Specifically, the prior art is deficient in methods of treating breast cancer by excising the tumor and ablating the margin of the tumor in a minimally invasive manner. The present invention fulfills this long-standing need and desire in the art.

SUMMARY OF THE INVENTION

The present invention is directed to a method for treatment of a cancerous lesion in an individual. The method comprises excising the cancerous lesion under open guidance or imaging guidance to form a first margin around the bed of the excised lesion. The first margin is ablated to obtain a second cancer-free margin around the bed of the excised lesion. The present invention is directed to a method comprising the further step of diagnosing a cancer as a presence of the cancerous lesion or determining the extent of the cancerous lesion via imaging thereof or a combination thereof. The extent of the cancerous lesion may be determined after diagnosis via the same imaging.

The present invention also is directed to a related method further comprising determining ablation parameters by intravascularly administering a fluorophore to the individual prior to ablating the second margin. Fluorescence of the fluorophore is measured prior to ablating the second margin and as the second margin is ablated and a decrease in the fluorescence is correlated with an increase in the parameters.

The present invention also is directed to another related method further comprising diagnosing the cancer by locating a site of interest in a tissue via mammography, MRI or ultrasound imaging thereof and obtaining a core sample of the tissue at the site of interest. Cytology is used to determine if the core sample comprises a cancerous lesion.

The present invention also is directed to another related method for treatment of a cancerous lesion in a breast of an individual. The method further comprises locating a potentially cancerous lesion in the breast tissue via imaging thereof and obtaining a core sample from the lesion immediately prior to excision of the lesion or immediately after excision of the lesion. The lesion is diagnosed as cancerous from a cytology sample prepared from cells from the core. The cancerous lesion is excised under open guidance or imaging guidance to form a first margin around the bed of the excised lesion. The first margin is ablated to obtain a second cancer-free margin around the bed of the excised lesion. Diagnosing the lesion as cancerous immediately prior to or immediately after excision provides for minimally invasive, same day treatment for the cancerous lesion. Further to this method the present invention is directed to a determination of the extent of the cancerous lesion via imaging thereof. Additionally, as described supra, the method further comprises determining ablation parameters of the margin.

The present invention is directed further to a method of treating a close or positive margin of an excisional site of a cancerous lesion in a breast of an individual. The close or positive margin of the excisional site is located via imaging thereof whereupon a fluorophore is administered intravascularly to the individual and the fluorescence of the fluorophore is measured at the excisional site. A second margin is ablated with a radiofrequency probe under guided imaging and fluorescence of the fluorophore is measured as the second margin is ablated. A decrease in the fluorescence correlates with an increase in ablation of the close or positive margin to form a second cancer free margin thereby treating the close or positive margin.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

In one embodiment of the present invention, there is provided a method for treatment of a cancerous lesion in an individual, comprising excising the cancerous lesion under open guidance or imaging-guidance to form a first margin around the bed of the excised lesion; and ablating the first margin to obtain a second cancer-free margin around the bed of the excised lesion, thereby treating the cancerous lesion.

Further to this embodiment the method comprises determining ablation parameters comprising depth of the second margin or of volume of tissue ablated to form the second margin or a combination thereof. In an aspect of this further embodiment, ablation parameters may be determined by intravascularly administering a fluorophore to the individual prior to ablating the second margin; measuring fluorescence of the fluorophore prior to ablating the second margin and as the second margin is ablated; and correlating a decrease in the fluorescence with an increase in the parameters. A representative example of a fluorophore is a fluorescent dye.

In another further embodiment the method comprises diagnosing the cancer as a presence of the cancerous lesion. In an aspect of this further embodiment, diagnosis of the cancer may comprise locating a site of interest in a tissue via mammography, MRI or ultrasound imaging thereof; obtaining a core sample of the tissue at the site of interest; and determining if the tissue sample comprises a cancerous lesion. Further to this aspect the method may comprise determining the extent of the cancerous lesion after diagnosis thereof via the imaging techniques.

In aspects of this further embodiment determining if the core sample is cancerous comprises performing cytology on the core sample prior to excising the cancerous lesion or performing touch preparation cytology on the core sample obtained after excising the cancerous lesion. Further to this aspect the cytological technique is performed on the same day as the excision and the ablation of the cancerous lesion.

In all aspects of this embodiment the cancerous lesion may be excised via percutaneous excision or open excision during a lumpectomy thereof. The cancerous lesion may have a diameter of about 2.0 cm or less and is excised via percutaneous excision or open excision. Alternatively, the cancerous lesion may have a diameter greater than 2.0 cm and is excised via open excision.

In one aspect of this embodiment the second margin may be ablated via an ablative device that delivers direct or indirect heating. The device may deliver direct or indirect heat via radiofrequency ablation, interstitial laser photocoagulation, or ultracision with a harmonic scapel. In another aspect ablating the second margin may be via cryotherapy. In all aspects of this method the cancerous lesion may comprise a breast cancer. Furthermore, imaging may be performed via mammography, MRI or ultrasound imaging.

In a related embodiment of the present invention there is provided a method for minimally invasive, same day diagnosis of and treatment of a cancerous lesion in a breast of an individual, comprising locating a potentially cancerous lesion in the breast tissue via imaging thereof; obtaining a core sample from the lesion immediately prior to excision of the lesion or immediately after excision of the lesion; and diagnosing the lesion as cancerous from a cytology sample prepared from cells from the core; excising the cancerous lesion under open guidance or imaging guidance to form a first margin around the bed of the excised lesion; and ablating the first margin to obtain a second cancer-free margin around the bed of the excised lesion, where diagnosing the lesion as cancerous immediately prior to or immediately after excising the cancerous lesion provides for same day treatment thereof.

Further to this embodiment, the method comprises determining the extent of the cancerous lesion via imaging thereof and/or determining ablation parameters both as described supra. In all aspects of this embodiment imaging, cytology, excisional and ablative techniques, the fluorophore, and the size of the cancerous lesion in the breast are as described supra.

In another embodiment of the present invention, there is provided a method of treating a close or positive margin of an excisional site of a cancerous lesion in a breast of an individual, comprising locating the close or positive margin of the excisional site via imaging thereof; intravascularly administering a fluorphore to the individual; measuring fluorescence of the fluorphore at the excisional site; ablating a second margin with a radiofrequency probe under guided imaging; measuring fluorescence of the fluorophore as the second margin is ablated; and correlating a decrease in the fluorescence with an increase in ablation of the close or positive margin to form a second cancer-free margin thereby treating the close or positive margin.

In all aspects of this embodiment the excisional site may be a percutaneous excisional site or an open excisional site. Also, the fluorophore may be a fluorescent dye. Imaging may be performed by MRI or ultrasound imaging.

The present invention provides a method of tumor bed ablation after excision. Generally the method may be used on cancerous lesions or tumors of a size amenable to lumpectomy. The method may be used to ablate margins of small breast lesions with diameters about 2.0 cm or less after percutaneous or open excision or, alternatively, the method may be used to ablate margins of larger lesions or tumors with diameters greater than 2.0 cm after open excision. The method provides comprehensive, minimally invasive, same-day diagnosis and treatment for patients with small lesions that are treated via percutaneous or open excision coupled with ablation to obtain a margin. Although preferably occurring as a same day treatment, ablation of tumor bed margins on larger breast lesions could occur more than one day after excision.

The treatment method utilizes devices for tumor excision and techniques for margin ablation all known to one of skill in the art. The method uses standard imaging techniques to predict the extent of the disease and to guide the removal of the lesion or tumor. Diagnostic methods may be standard cytology methods. Methods to determine the extent of margin ablation may use fluorescence measurements of a fluorophor administered to a patient such as are standard in the art. Moreover, one of skill in the art would recognize that the treatment method disclosed herein is also applicable to other cancers besides breast cancer.

The tumor or lesion may be removed via percutaneous excision or through open excision. Excisional devices are well known in the art. For example, although not limited to, a Mammotome® Breast Biopsy System may be used to percutaneously excise or resect abnormal tissue. The Mammotome® Breast Biopsy System is a well-established diagnostic tool that allows more accurate diagnosis and permits removal of larger specimens than is possible with core biopsy. The Mammotome® Breast Biopsy System is a minimally invasive, image guided procedure, either stereotactically guided or guided via ultrasound, that helps physicians locate breast abnormalities and obtain tissue samples for diagnosis. This treatment paradigm is potentially more accurate than surgery.

Core needle biopsy limits the amount of tissue available to pathologists for establishing the histologic diagnosis and biochemical markers. A core biopsy may show ductal carcinoma in situ, but the final pathology of the lumpectomy specimen may demonstrate focal areas of infiltrating carcinoma. In contrast, the Mammotome® System or similar devices uses single-insertion technology with vacuum assistance for removal of an imaged abnormality via a sutureless incision.

The Mammotome® Breast Biopsy System procedure can be performed through a ⅛" skin incision in less than one hour under a local anesthetic. The Mammotome® is capable of sampling a variety of breast abnormalities, such as microcalcifications, asymmetric densities, solid masses or nodules. It can obtain multiple tissue samples for pathologic analysis with one insertion, whereas other methods require multiple insertions. A procedure which requires no sutures, the Mammotome® is a valuable tool that helps physicians accurately diagnose breast cancer in its earliest stages.

In stereotactic procedures, the patient lies face down on a special table with the breast protruding through a hole in the table. The breast is lightly compressed to immobilize it. This table is also a mammogram table that allows the physician to get a clear mammographic image of the area to be sampled. The table is connected to a computer that processes digital images. Placement of the sampling device is guided by a computerized system using x-rays.

Detection of breast lesions or tumors is via standard methods such as mammography or other imaging systems, e.g., MRI or ultrasound. Imaging techniques are used to predict the extent of the disease, guide the removal of the tumor and document ablation zone. For example, MRI of the breast using the RoDEO (Rotating Delivery of Excitation Off-resonance) pulse sequence recently has been developed to diagnose and determine the extent of local breast cancer. Validation studies comparing breast Rotating Delivery of Excitation Off-resonance MRI to serially sectioned mastectomy specimens showed a high degree of correlation in the ability of Rotating Delivery of Excitation Off-resonance MRI to predict disease extent and lesion margins.

Diagnosis of tissue samples is obtained via standard cytological techniques. Core samples may be obtained percutaneously or by a standard excisional breast biopsy. Diagnosis may be performed prior to percutaneous or open excision or after excision. To provide same-day treatment to patients, pre-procedure cytology, e.g. fine needle cytology, is performed prior to percutaneous excision or intra-procedure touch preparation cytology is performed after excision. Either method can be used for immediate diagnosis of lesions. The touch-prep method, which involves touching the specimen to a glass slide to which tumor cells will adhere, allows simple, quick, e.g., 2-3 minutes, safe with no loss of diagnostic material, and accurate diagnosis at the time of surgery.

The present invention uses ablation techniques and devices that use direct or indirect heat known to one skilled in the art to obtain a clear tumor margin. Ablation of margins can be accomplished by, but not limited to, radiofrequency ablation, interstitial laser photocoagulation or ultracision with the harmonic scalpel or other methods using direct or indirect heat. Alternatively, ablation of margins may be accomplished via cryotherapy.

Figure 1:
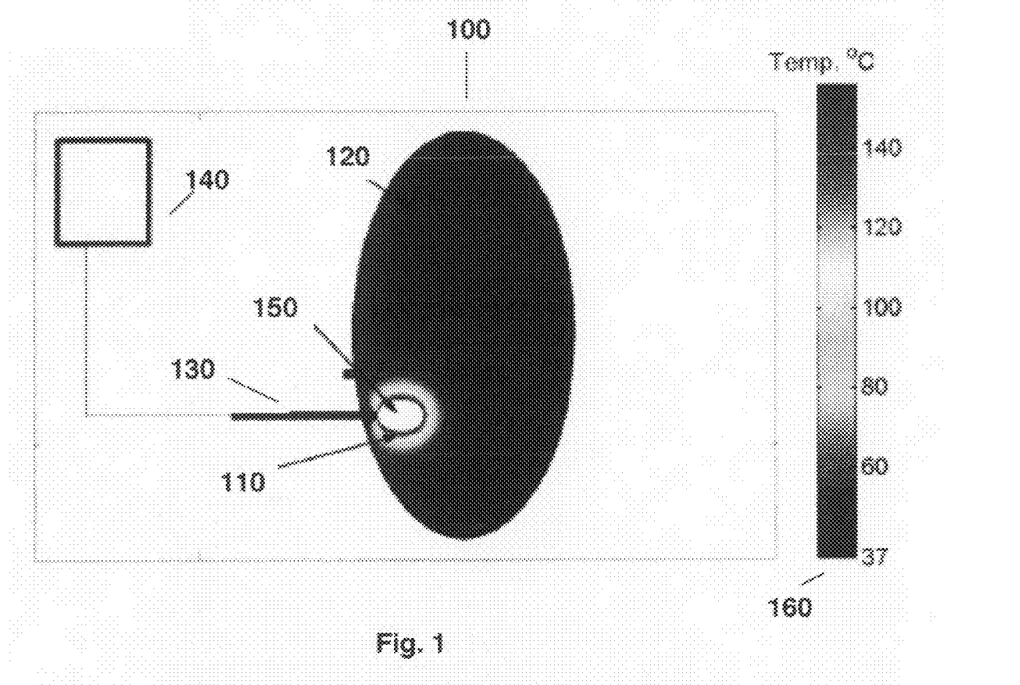
FIG. 1 is a schematic 100 demonstrating ablation of margins 110 in a breast 120 using direct or indirect heat from e.g., a radiofrequency probe 130 connected to a control panel 140, after excision of the breast lesion to form a tissue cavity 150. A scale 160 depicts tissue temperature at various locations.

As described herein, radiofrequency ablation is preferred (FIG. 1). As used herein, radiofrequency ablation is based on time and temperature rather than impedance. For example, a radiofrequency probe, may be operated at a power of 150 W and tissue temperature at the margin may be kept at 100° C. for 15 min to ablate the margin.

Preferably, ablation of the margin is done at the time of surgery, but also can be done under open guidance or image guidance after an excision of any type, i.e., open excision or percutaneous excision, to ablate a positive margin or obtain a margin of ablated tissue or tumor-free zone around the resected tumor. Ablation of the margin instead of excision thereof avoids pathological problems involved with intraoperative establishment of negative or close margins which are inaccurate. Pathology only can give an estimate of the margin.

Thus, ablating the margins avoids second surgeries for close or positive margins found on permanent pathology several days later. For example, in the United States nearly 40% (20-75%) of patients go back to the operating room for a second surgery for close or positive margins (12). Thus the present invention has value in simply treating close or positive margins, such that those patients that have to go back to the operating room do so only for much more extensive disease requiring mastectomy.

The present invention also provides a method of intraoperatively measuring and confirming ablation parameters or a combination of parameters, such as the depth of ablation and the volume of ablated tissue to form a cancer free margin by measuring fluorescence of a fluorophor or fluorescent substance at the cavity site. A fluorescent biocompatible substance such as, although not limited to, a fluorescent dye, e.g. a green dye or other useful fluorescent dyes well known to a person having average ability in this art, is administered intravenously to the patient. The fluorescent dye or other fluorophor is retained in the vasculature bound to protein. Fluorescence measurements are obtained from the vascularized tissues in the excised cavity prior to and after ablation of a cancer-free margin. Laser light in conjunction with a filter appropriate for the fluorescent dye are used to measure fluorescence of the dye. Mathematical modeling is used to calculate the depth of ablation and volume of ablated tissue from the fluorescence measurements.

Additionally, it is contemplated that ablation of the margin subsequent to excision obviates the need for radiation therapy, typically a six-week course of treatment. Currently, the standard of care is whole breast radiation or, alternatively, brachytherapy which is local radiation given to the breast cancer cavity site. During brachytherapy, a balloon is implanted at the time of surgery or multiple needles are inserted into the breast and remain approximately a week. Both methods require thrice daily insertion of radioactive seeds to treat the breast and subsequent removal of the devices.

Given that 90% of local breast recurrence is in the bed of the original tumor (12) and that 5-year follow-up of multiple small series of different types of partial breast irradiation show no difference in local recurrence rate from whole breast irradiation, those of ordinary skill in the art accept partial breast irradiation as equal to whole breast irradiation (13-15). As the present invention provides a method of actually measuring the depth of the ablation zone and demonstrates the lack of recurrence in patients, it is contemplated that ablation of the breast cancer excision site is equivalent to brachtherapy and is a better alternative to radiation therapy in selected patients with favorable tumors or in addition to radiation therapy in patients with a high risk of recurrence. Therefore, ablation of the margin of a percutaneous or open excision site is superior to brachytherapy in terms of preventing local recurrence and cosmetic result.

Major benefits of the system disclosed herein include improved cosmetic result, reduced recovery time, and less stress for the patient as no waiting for a diagnosis or treatment decision is involved. In addition, a same-day diagnosis and treatment system also means lowered cost due to reduced hospital or same-day surgery time. Furthermore, as margin ablation replaces the need for radiation therapy, the methods described herein would be extremely beneficial to the debilitated and/or the working or poor rural patient as a same day treatment. The method also is attractive because of the superior cosmetic result and lack of side-effects from radiation therapy.

It is contemplated that total ablation of breast carcinoma would require the resolution of several problems prior to ablation being deemed as a definitive treatment modality for an intact carcinoma. Accurate 3-D pathologic reconstruction is needed to assure complete tumor ablation prior to breast carcinoma being treated by in situ ablation only. Follow-up imaging remains problematic, such as, ideal time to schedule, inability to differentiate post-treatment inflammatory changes from recurrence or untreated tumor and cost associated with MRI or other scans.

The following examples are given for the purpose of illustrating various embodiments of the invention and are not meant to limit the present invention in any fashion.

EXAMPLE 1

MRI-directed Interstitial Laser Photocoagulation

Preliminary results of MRI-directed interstitial laser photocoagulation in 30 patients with breast cancer indicated that the procedure was well-tolerated and side effects were similar to those of routine stereotactic needle biopsy. Each patient has between one and five ablation zones for a total of 68 treatment zones. When the entire 10-minute treatment session was completed, the pathology correlation determined effective cell death in all cases. The histologic determination of treatment zones by proliferating cell nuclear antigen (PCNA) staining within the tumor matched the MRI estimates of zone size in all cases (data not shown).

EXAMPLE 2

Excision and Ablation of Margin in Mastectomy Specimens

Figure 2:
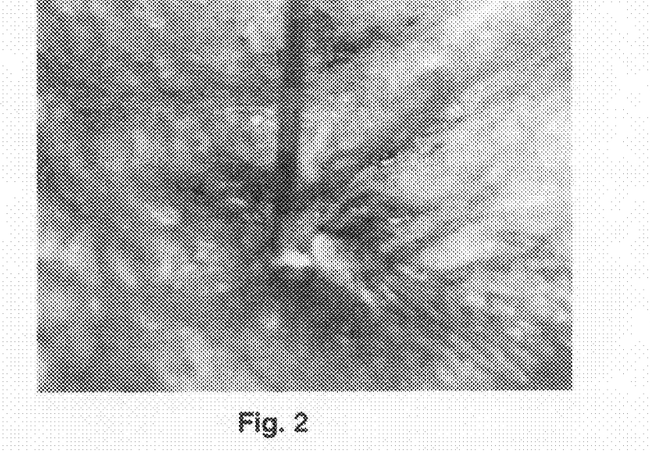
FIG. 2 depicts excision and margin ablation of normal breast tissue on a mastectomy specimen using radiofrequency.

Normal tissue was excised, under IRP-approved protocol, from 39 sites on mastectomy specimens. The sites were then ablated with radiofrequency to measure the margin produced around the cavity site (FIG. 2).

Tumors were excised percutaneously from 10 patients using the Mammotome®. The margin was ablated and then the site was excised for pathological examination. Adequate margins were obtained on all specimens examined (data not shown).

EXAMPLE 3

Figure 3A:
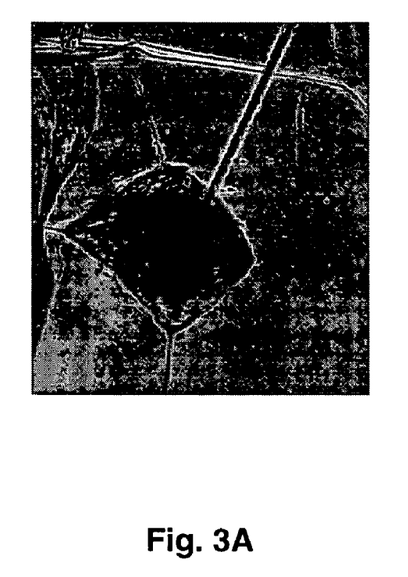
FIG. 3A depicts ablating a margin in a patient using direct or indirect heat from a radiofrequency probe (white arrow).

Excision and Ablation of Margin as Alternative to Excision and Radiation Therapy Because of debilitation of the patient and/or refusal of the patient to undergo radiation therapy, the treatment protocol of excision and radiation therapy is not a viable procedure. In 10 such patients, standard excision followed by ablation of the margin with radiofrequency was performed (FIG. 3A). The patients were followed-up closely over a 2-year period or less with no recurrences in any of them.

Figure 3B:
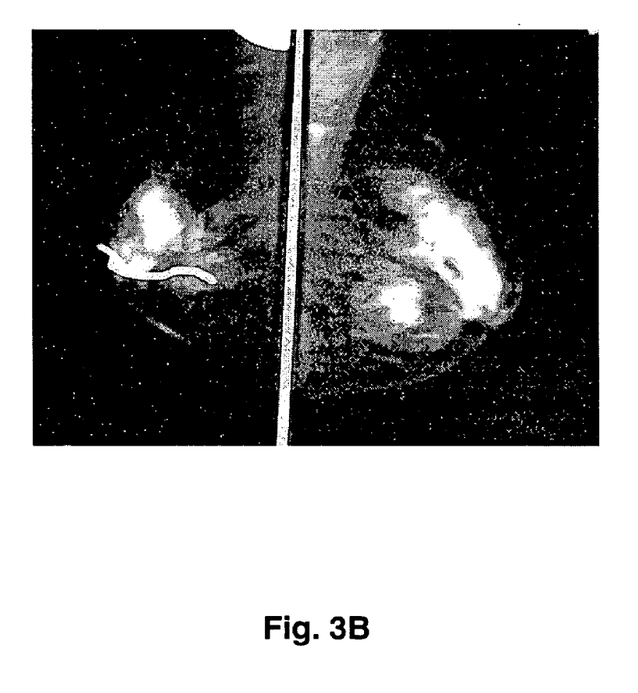
FIG. 3B is a mammogram of a patient taken two years after tumor excision with margin ablation was performed. No evidence of recurrence is found. A radio-opaque marker lies over the skin.

In one such instance an elderly woman with severe pulmonary disease who had a large right breast cancer removed was treated with radiofrequency ablation and follow-up. This patient demonstrates none of the typical visible side-effects of radiation therapy including retraction, swelling, erythema or browning of the skin. Two year mammograms show no evidence of recurrence (FIG. 3B). Two-year follow-up is emphasized since most recurrences for breast tumors occur in the first 2 years after treatment.

EXAMPLE 4

Fluorescence Measurement of Dye as a Marker of Ablation Depth

Figure 4:
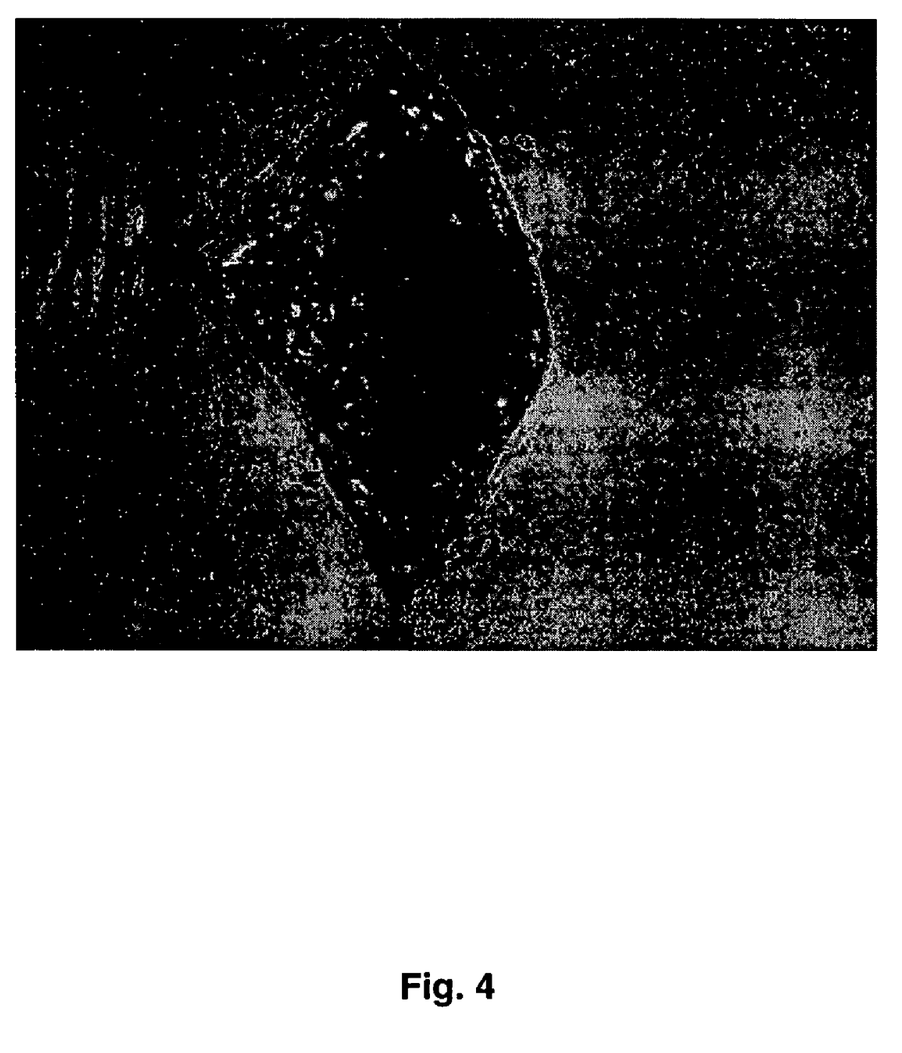
FIG. 4 depicts an excisional cavity in which no fluorescence can be seen grossly from the start (white arrow) to the depth of the ablation zone.

A green dye is administered intravascularly to the patient and fluorescence measured from the cavity before and after the ablation of breast tissue. This determines if the depth of ablation needed for breast conservation therapy is present. Using laser light in the cavity and a 815 nm filter, the ablated zone in the cavity is reconstructed to actually measure the depth of ablation (FIG. 4).

The following references are cited herein:
1. Kaufman et al. Am J Surg, 184:394-400 (2002).
2. Johnson et al. Am. J. Surg, 184:550-4 (2002).
3. Pfleiderer et al. Eur Radiol, 12:3009-14 (2002).
4. Tafra et al. Ann of Surg Onc, 10:1018-24 (2003).
5. Harms S, Mumtaz H, Hyslop B, et al. Soc Photo-Optical Instrumentation Engineers Proc, 3590:484-89 (1999).
6. Dowlatshahi et al. Arch Surg, 135:1345-52 (2000).
7. Hayashi et al. Am J Surg, 185:429-35 (2003).
8. Harms SE, Mumtaz H, Klimberg VS and Westbrook K. Breast Diseases: A Year Book Quarterly, 9:336-38 (1999).
9. Dowlatshahi K, Francescatti DS and Bloom KJ. Am J Surg, 184:359-63 (2002).
10. Singletary et al. Cancer J, 8:177-80 (2002).
11. Burback et al. Am Cancer Soc, 98:1369-76 (2003).
12. Henry-Tillman R, Johnson A T, Smith L F, and Klimberg V S. Semin Surg Oncol, 20(3):206-13 (April-May 2001).
13. Chen P, Vicini F, Kestin L, Wallace M, Mitchell C, Benitez P, Pettinga J, and Martinez A. In J Radiat Oncol Biol Phys, 57(2 Suppl):S309-10 (2003).
14. Edmundson G K, Weed D, vicini F, Chen P, and Martinez A. 57(2 Suppl):S307-10 (2003).
15. Perera F, Yu E. Engel J, et al. Int J Radiat Oncol Biol Phys 57(5):1239-46 (Dec. 1, 2003).

Any patents or publications mentioned in this specification are indicative of the levels of those skilled in the art to which the invention pertains. Further, these patents and publications are incorporated by reference herein to the same extent as if each individual publication was specifically and individually incorporated by reference.

One skilled in the art will appreciate readily that the present invention is well adapted to carry out the objects and obtain the ends and advantages mentioned, as well as those objects, ends and advantages inherent herein. The methods and procedures described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for treatment of a cancerous lesion in an individual with breast cancer, comprising:
   excising the cancerous lesion under open guidance or imaging guidance to form a first margin around the bed of the excised lesion;
   ablating said first margin to obtain a second cancer-free margin around the bed of the excised lesion;
   intravascularly administering a fluorescent dye to the individual at the excisional site prior to ablating said second margin;
   measuring fluorescence of said fluorescence dye prior to ablating said second margin and as said second margin is ablated;
   correlating a decrease in said fluorescence with an increase in ablation parameters, wherein said correlating comprises:
   determining ablation parameters including both depth of the second margin and volume of tissue ablated to obtain second said margin, thereby treating the cancerous lesion.

2. The method of claim 1, further comprising: diagnosing that cancer is present in the lesion.

3. The method of claim 2, wherein diagnosing said cancer comprises:
   locating a site of interest in a tissue via mammography, MRI or ultrasound imaging thereof;
   obtaining a core sample of said tissue at the site of interest; and
   determining if said core sample comprises cancerous cells.

4. The method of claim 3, wherein determining if said core sample is cancerous comprises:
   performing cytology on said core sample prior to excising the cancerous lesion; or
   performing touch preparation cytology on said core sample obtained after excising said cancerous lesion.

5. The method of claim 3, wherein diagnosing said cancer is performed on the same day as the excision and the ablation of said cancerous lesion.

6. The method of claim 3, further comprising: determining the extent of the cancerous lesion after diagnosis thereof via said imaging.

7. The method of claim 1, wherein said imaging is mammography, MRI or ultrasound imaging.

8. The method of claim 1, wherein excising said cancerous lesion is via percutaneous excision or open excision during a lumpectomy thereof.

9. The method of claim 8, wherein said cancerous lesion has a diameter of about 2.0 cm or less and is excised via percutaneous excision or open excision.

10. The method of claim 8, wherein said cancerous lesion has a diameter greater than 2.0 cm and is excised via open excision.

11. The method of claim 1, wherein ablating said second margin is via an ablative device to deliver heat directly or indirectly to the margin.

12. The method of claim 11, wherein said ablative device delivers indirect or direct heat via radiofrequency ablation, interstitial laser photocoagulation, or ultra scission with a harmonic scalpel.

13. The method of claim 1, wherein ablating said second margin is via cryotherapy.

14. A method for minimally invasive, same day diagnosis of and treatment of a cancerous lesion in a breast of an individual, comprising:
- locating a potentially cancerous lesion in the breast tissue via imaging thereof;
- obtaining a core sample from the lesion immediately prior to excision of said lesion or immediately after excision of said lesion;
- diagnosing said lesion as cancerous from a cytology sample prepared from cells from the core;
- excising the cancerous lesion under open guidance or imaging guidance to form a first margin around the bed of the excised lesion;
- ablating said first margin to obtain a second cancer-free margin around the bed of the excised lesion;
- intravascularly administering a fluorescent dye to the individual at the excisional site prior to ablating said second margin;
- measuring fluorescence of said fluorescent dye prior to ablating ablation second margin and as the second margin is ablated;
- correlating a decrease in said fluorescence with an increase in the parameters, wherein said correlating comprises:
- determining ablation parameters including both depth of the second margin and volume of tissue ablated to obtain the second margin; wherein diagnosing said lesion as cancerous immediately prior to or immediately after excising said cancerous lesion provides for same day treatment thereof.

15. The method of claim 14, further comprising: determining the extent of said cancerous lesion via imaging thereof.

16. The method of claim 15, wherein said imaging is mammography, MRI or ultrasound imaging.

17. The method of claim 14, wherein said imaging is mammography, MRI or ultrasound imaging.

18. The method of claim 14, wherein cytology of said sample obtained after excision of the lesion is touch preparation cytology.

19. The method of claim 14, wherein excising said cancerous lesion is via percutaneous excision or open excision during a lumpectomy thereof.

20. The method of claim 19, wherein said cancerous lesion has a diameter of about 2.0 cm or less and is excised via percutaneous excision or open excision.

21. The method of claim 19, wherein said cancerous lesion has a diameter greater than 2.0 cm and is excised via open excision.

22. The method of claim 14, wherein ablating said second margin is via an ablative device delivering heat directly or indirectly to the margin.

23. The method of claim 22, wherein said ablative device delivers indirect or direct heat via radiofrequency ablation, interstitial laser photocoagulation, or ultra scission with a harmonic scalpel.

24. The method of claim 14, wherein ablating said second margin is via cryotherapy.

25. A method of treating a close or positive margin of an excisional site of a cancerous lesion in a breast of an individual, comprising:
- locating the close or positive margin of the excisional site via imaging thereof;
- intravascularly administering a fluorescent dye to the vasculature of the excisional site in the individual;
- measuring fluorescence of the fluorescent dye in the vasculature at the excisional site;
- ablating a second margin with a radiofrequency probe under guided imaging;
- measuring fluorescence of said fluorophore as the second margin is ablated; and
- correlating a decrease in said fluorescence with an increase in ablation of the close or positive margin to form a second cancer free margin thereby treating said close or positive margin.

26. The method of claim 25, wherein said excisional site is a percutaneous excisional site or an open excisional site.

27. The method of claim 25, wherein said imaging is MRI or ultrasound imaging.

* * * * *